United States Patent
Toso

[11] Patent Number: 5,645,080
[45] Date of Patent: Jul. 8, 1997

[54] WAIST SUPPORTED CARRYING CASE INCLUDING A BACK SUPPORT

[76] Inventor: Victor Toso, 771 Harding St., NE., Minneapolis, Minn. 55413

[21] Appl. No.: 666,625

[22] Filed: Jun. 18, 1996

[51] Int. Cl.⁶ .................................................. A61F 5/37
[52] U.S. Cl. ............................ 128/876; 5/633; 602/19
[58] Field of Search ........................... 128/846, 869, 128/873, 874, 875, 876; 602/19; 2/311, 312, 315, 317, 319; 5/633, 634

[56] References Cited

U.S. PATENT DOCUMENTS

| | | | |
|---|---|---|---|
| 3,143,748 | 8/1964 | Manning | 5/344 |
| 4,132,229 | 1/1979 | Morrison | 128/826 |
| 4,185,673 | 1/1980 | Daniello | 5/653 |
| 4,190,918 | 3/1980 | Harvell | 5/465 |
| 4,627,109 | 12/1986 | Carabelli et al. | 2/44 |
| 4,738,545 | 4/1988 | Westgor | 383/4 |
| 4,773,106 | 9/1988 | Toso et al. | 5/432 |
| 4,813,080 | 3/1989 | Toso | 2/94 |
| 5,001,791 | 3/1991 | Toso | 5/432 |
| 5,083,554 | 1/1992 | Toso | 128/78 |
| 5,452,476 | 9/1995 | Jenks | 2/311 |
| 5,547,461 | 8/1996 | Levis | 128/876 |

FOREIGN PATENT DOCUMENTS 2557780  1/1984  France .

*Primary Examiner*—Michael A. Brown
*Attorney, Agent, or Firm*—Aquilino & Welsh

[57] ABSTRACT

A waist supported carrying case including a therapeutic back support for supporting the lower back region of a user in a seated position. The carrying case includes a belt for securing the carrying case to the waist of an individual and a pouch assembly positioned on the belt. The pouch assembly includes at least one sleeve having a therapeutic back support therein.

20 Claims, 8 Drawing Sheets

WAIST SUPPORTED CARRYING CASE INCLUDING A BACK SUPPORT

BACKGROUND OF THE INVENTION

1. Field of the Invention

The present invention relates to waist supported carrying cases, commonly referred to as fannypacks, including a therapeutic support device. More particularly, the invention relates to waist supported carrying cases including a back support for supporting the lower back of a person in a seated position.

2. Description Of The Prior Art

Individuals must often sit upright on a variety of flat surfaces without a rigid back support. For example, individuals may be forced to sit on the ground or floor, or on a backless chair, bench, and the like, for extended periods of time. Sitting in this manner is generally uncomfortable, painful and difficult. These problems are further exaggerated for individuals with back problems.

Activities were individuals may be forced to sit without a rigid back support include, but are not necessarily limited to, athletic events such as hunting, boating, camping and so forth. Other passive events such as watching athletic contests, meditating and even listening to music may cause back strain when one position is maintained for a considerable length of time.

The problems associated with sitting in this manner are addressed in my prior U.S. Pat. Nos. 4,773,106, 4,813,080 and 5,001,791, which are incorporated herein by reference. The patents disclose back support devices enabling an individual to support his or her back when the individual must sit upright without an adequate back support.

The present invention represents an improvement over the known prior art by providing a back support that may be carried with an individual in a convenient manner. Accordingly, a back support is combined with a waist supported carrying case to facilitate carrying of the device when used for various activities as described hereinabove. The waist supported carrying case permits an individual to carry the back support in a convenient, yet accessible, manner. As a result, individuals are more likely to take advantage of the back support and avoid unnecessary pain.

SUMMARY OF THE INVENTION

It is, therefore, an object of the present invention to provide a waist supported carrying case including a therapeutic back support for supporting the lower back region of a user in a seated position. The carrying case includes a belt for securing the carrying case to the waist of an individual and a pouch assembly positioned on the belt. The pouch assembly includes at least one sleeve having a therapeutic back support therein.

It is also an object of the present invention to provide a carrying case including a therapeutic back support wherein the back support is integrally formed within the at least one sleeve.

It is another object of the present invention to provide a carrying case including a therapeutic back support wherein the back support includes a rectangular back supporting member secured to the pouch assembly, the back support member having a length substantially spanning the width of the lower back of the user and a width substantially spanning the height of the lumber portion of the user. The back support further includes elongated straps attached to and extending from the pouch assembly, the straps forming loops and being of such a length to engage the knees of the user when the user is in a seated position whereby the force of the knees of the user on the straps pulls the back supporting member against the back of the user.

It is a further object of the present invention to provide a carrying case including a therapeutic back support wherein a seat pad is integrally stored within the pouch assembly.

It is also an object of the present invention to provide a carrying case including a therapeutic back support wherein the pouch assembly includes means for opening and closing the at least one sleeve to selective utilize the back support member.

It is another object of the present invention to provide a carrying case including a therapeutic back support wherein the back support is removably stored within the at least one sleeve.

It is a further an object of the present invention to provide a carrying case including a therapeutic back support wherein the pouch assembly includes a plurality of pockets for storing items.

It is also an object of the present invention to provide a carrying case including a therapeutic back support wherein the pocket assembly is secured between a first belt member and a second belt member, and the first belt member and the second belt member are respectively provided with cooperating locking members for securing the carrying case about the waist of a user.

It is another object of the present invention to provide a method for supporting the lumbar region of a user in a seated position. The method includes the following steps: positioning a carrying case about the waist of a user, wherein the carrying case includes a therapeutic back support for supporting the lower back region of a user in a seated position, and the back support includes a generally rectangular supporting member having a length substantially spanning the width of the lower back of the user and a width substantially spanning the height of the lumber portion of the user, elongated straps attached to and extending from the ends of the back supporting member, the straps forming loops being of such a length to engage the knees of the user when the user is in a seated position whereby the force of the knees of the user on the straps pulls the back supporting member against the back of the user, supporting the back of the user; locating the support member on the lumbar region of the user; positioning the straps about the knees of the user; and exerting an outward force with the knees against the straps to thereby pull the support member against the lumbar region and support the lumber region.

It is a further object of the present invention to provide a waist supported carrying case including a belt for securing the carrying case to the waist of an individual, a pouch assembly positioned on the belt, and a seat pad secured to, and stored within, a sleeve formed in the pouch. The seat pad is stored such that the seat pad may be withdrawn from the pouch assembly and positioned between an individual and a support surface when the individual plans to sit.

These and other objects and advantages of the present invention will become apparent from the following detailed specification when viewed in conjunction with the accompanying drawings.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
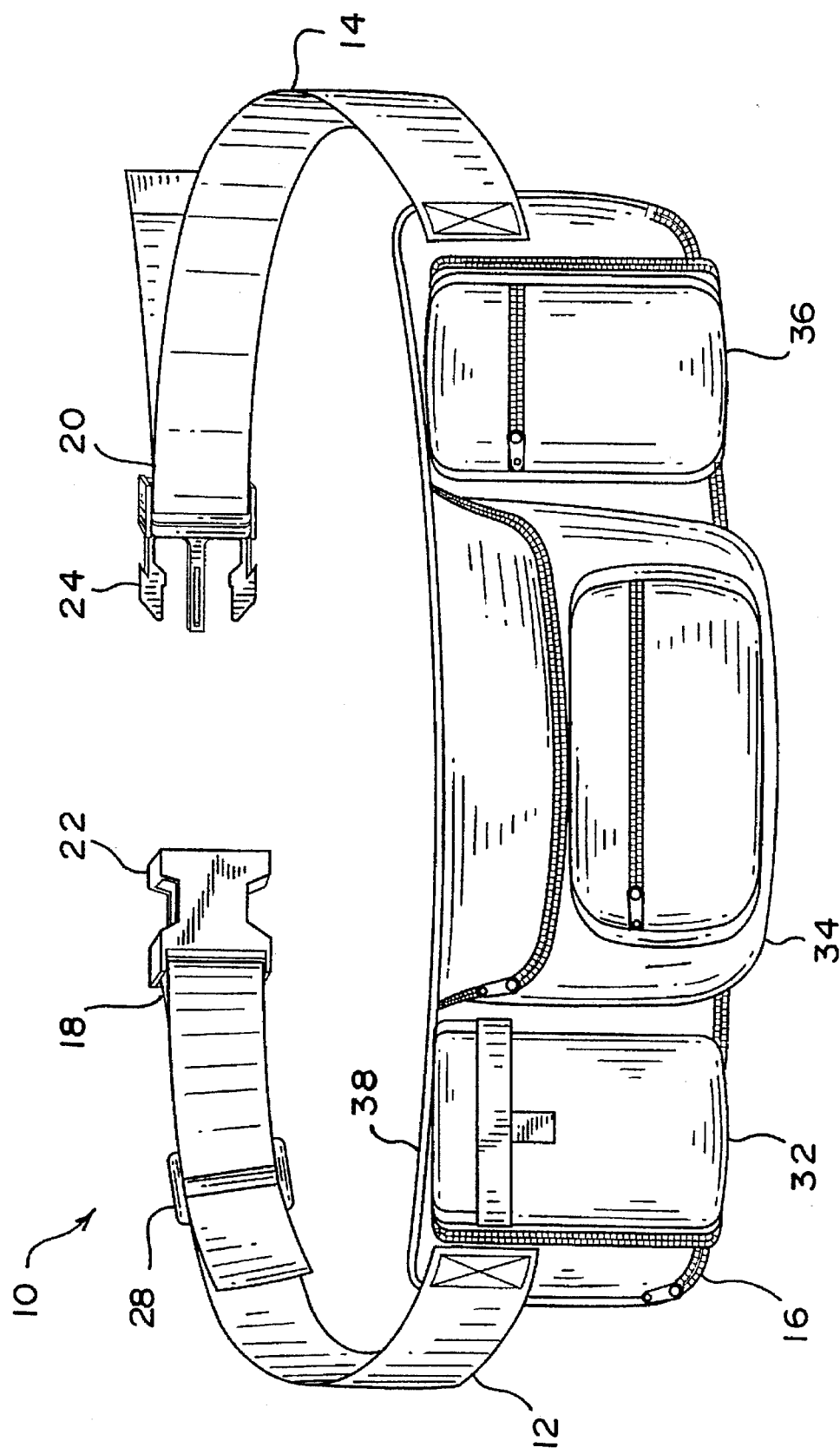
FIG. 1 is a perspective view showing the outer portion of the waist supported carrying case.
Figure 2:
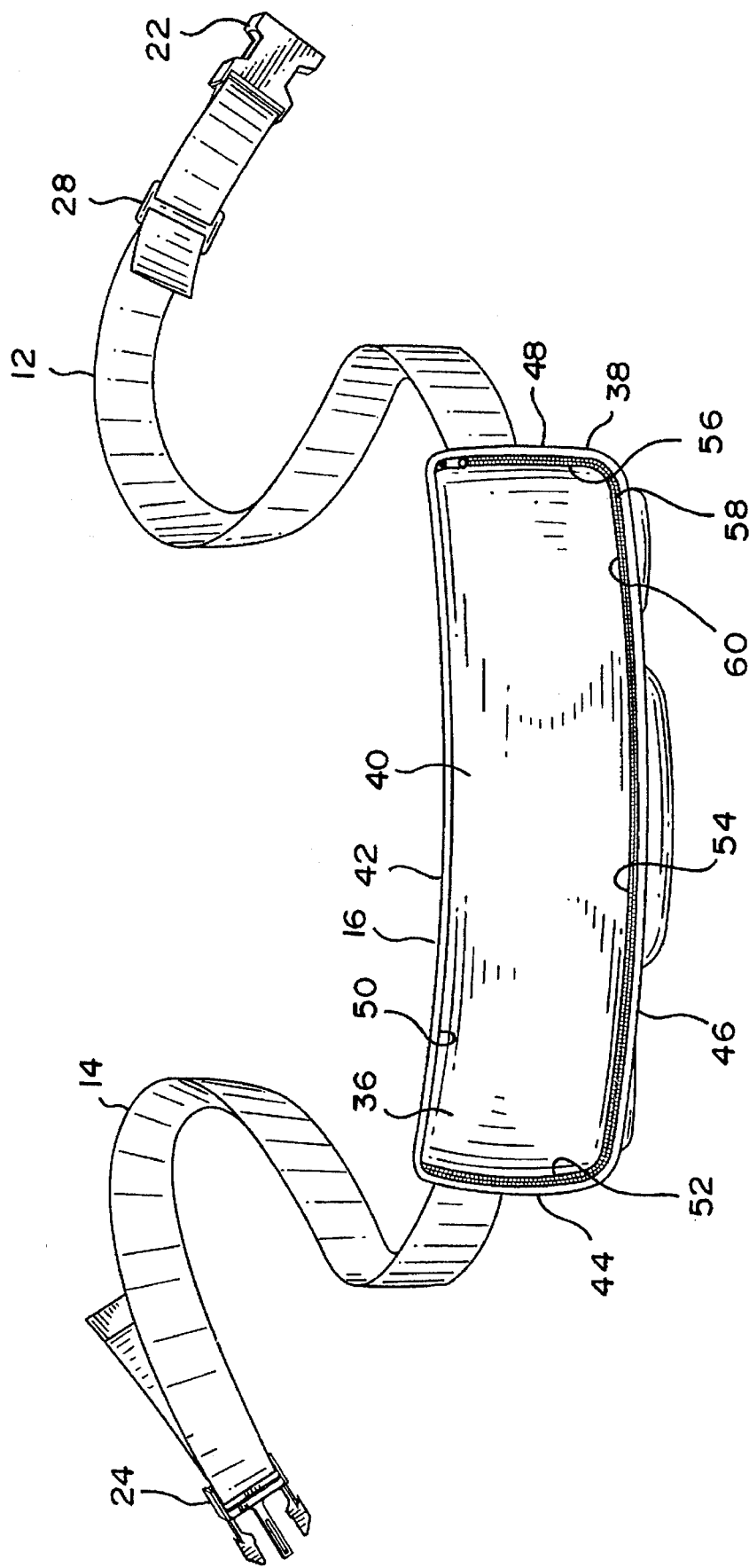
FIG. 2 is a perspective view showing the inner portion of the waist supported carrying case.
Figure 3:
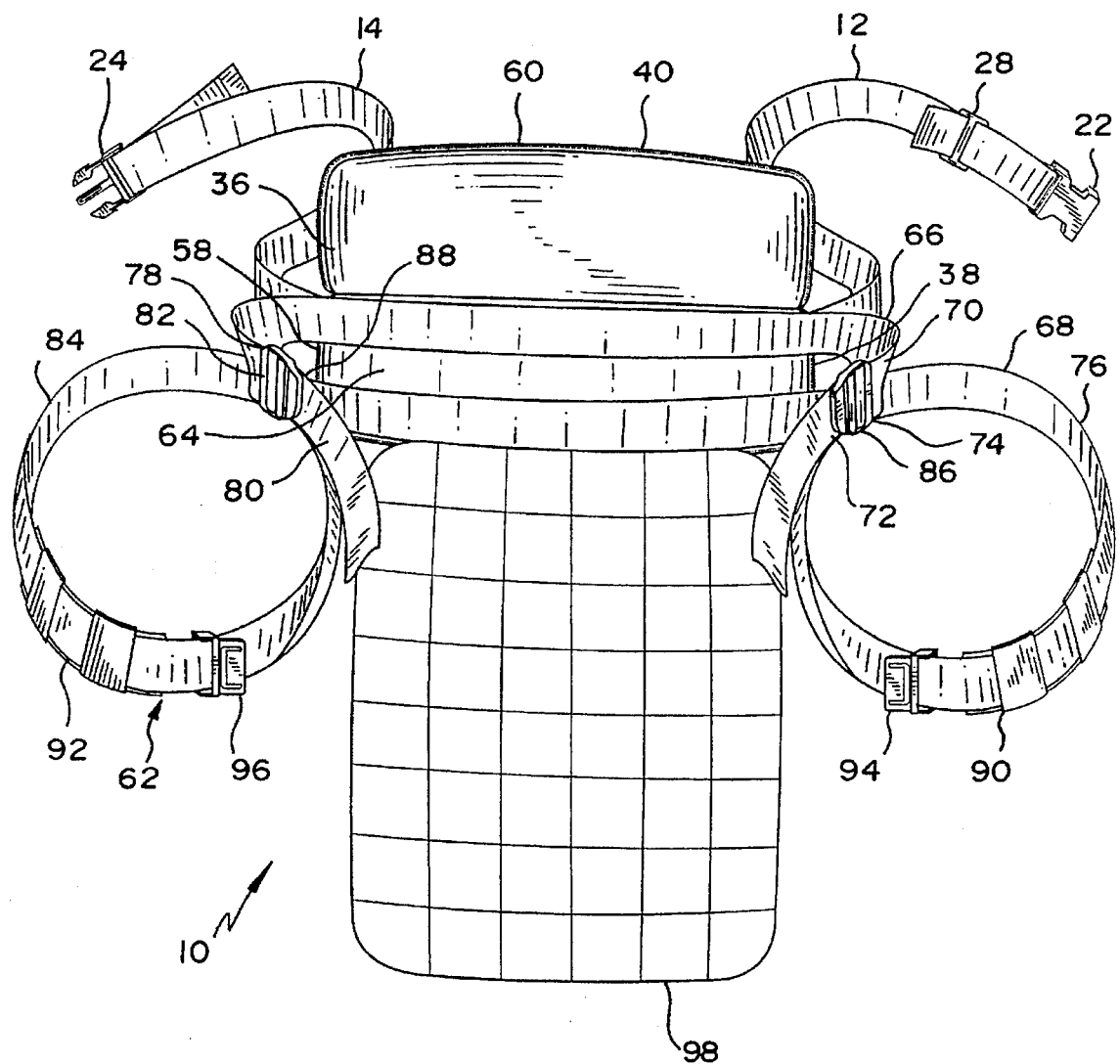
FIG. 3 is a perspective view showing the waist supported carrying case with the central sleeve opened.

Referring to FIGS. 1-3, the present waist supported carrying case 10 is disclosed. As is commonly understood in the art, the present waist supported carrying case includes a first belt member 12 and a second belt member 14 secured at opposite ends of a pouch assembly 16. The first belt member 14, the second belt member 14 and the pouch assembly 16 are arranged to form a belt that may be secured around the waist of an individual. With this in mind, the free ends 18, 20 of the first belt member 12 and the second belt member 14 are respectively provided with cooperating first and second locking members 22, 24. While the disclosed waist supported carrying case includes distinct elements (i.e., a first belt member, a second belt member, and a pouch assembly) connected to form the waist supported carrying case, it will be understood by those of ordinary skill in the art that the waist supported carrying case could be constructed in a variety of manners without departing from the spirit of the present invention.

Adjustment of the first belt member 12 and the second belt member 14 to fit individuals having various waist sizes is achieved by the provision of a releasable locking clasp 26 on the locking member 24 of the second belt member 14. The locking clasp 26 permits an individual to draw the second belt member 24 therethrough and lock the second locking member 24 at a specific location on the second belt member 14. In addition, the first belt member 12 is provided with a locking clasp 28 permitting adjustment of the length of the first belt member 12. The adjustment structures on the first and second belt members permit an individual to adjust the length of the waist supported carrying case to fit comfortably about the waist of an individual. It should be understood that a wide variety of adjustment mechanisms are known in the art, and could be applied to the disclosed waist supported carrying case without departing from the spirit of the present invention.

The pouch assembly 16 includes a variety of pockets 30, 32, 34 shaped to hold different objects. The shapes of these pockets may be varied to accommodate the needs of different individuals without departing from the spirit of the present invention.

With reference to FIGS. 2 and 3, the pouch assembly 16 is provided with a central sleeve 36. The central sleeve 36 defined by the space between the outer section 38 of the pouch assembly 16 and the inner section 40 of the pouch assembly 16. Specifically, the outer section 38 includes a first edge 42, a second edge 44, a third edge 46, and a fourth edge 48, and the inner section 40 includes a first edge 50, a second edge 52, a third edge 54, and a fourth edge 56. The first edge 42 of the outer section 38 is secured to the first edge 50 of the inner section 40 by sewing the edges together, or connecting the edges in any other conventional manner. The respective second, third and fourth edges of the outer section 38 and the inner section 40 are provided with cooperating zippers 58, 60. As a result, the outer section 38 and the inner section 40 may be selectively secured along their respective edges to form the closed central sleeve 36. When an individual wishes to open the central sleeve 36 and retrieve the contents of the sleeve, he or she simply unzips the edges to open the central sleeve 36 and remove the contents of the central sleeve.

With reference to FIG. 3, where the waist supported carrying case 10 is shown with the central sleeve 36 open, a back support 62 for supporting the back of an individual in a seated position is stored within the central sleeve 36. When the waist supported carrying case 10 is arranged such that the central sleeve 36 is open, a back support member 64 having an elongated and generally rectangular shape is created by the outer section 38 and the inner section 40. As will be discussed in greater detail, the back support member 64 is designed for positioning adjacent the lower back region of an individual. The back support member 64 may be cushioned, or padded, and/or reinforced to provide sufficient strength to support the wearer's lower back.

A first elongated strap 66 and a second elongated strap 68 are integrally attached to the outer section 38 within the central sleeve 36. Preferably, the straps are secured to the back support member 64 and extend outwardly from the second and fourth edges of the outer section 38. The first end 70 of the first strap 66 is secured to the first end 72 of the second strap 68 by a first buckle 74 to form a first loop 76. Similarly, the second end 78 of the first strap 66 is secured to the second end 80 of the second strap 68 by a second buckle 82 to form a second loop 84. Specifically, the first loop 76 is formed by securely attaching the first end 70 of the first strap 66 to the first buckle 74 and passing the first end 72 of the second strap 68 through a releasable locking clasp 86 on the first buckle 74. In this way, the length of the first loop 76 is readily adjusted by selectively drawing the first end 72 of the second strap 68 through the releasable locking clasp 86. Similarly, the second loop 84 is formed by securely attaching the second end 78 of the first strap 66 to the second buckle 82 and passing the second end 80 of the second strap 68 through a releasable locking clasp 88 on the second buckle. In this way, the length of the second loop 84 is readily adjusted by selectively drawing the second end 80 of the second strap 68 through the releasable locking clasp 88.

The first loop 76 and the second loop 84 are each provided with a pad 90, 92. Respective pads are secured to each loop such that the pad may move along the length of the loop to properly position the pad at the knee of a user. The pads lessen the strain on the user's knees, permitting the user to exert sufficient force on the back support member to hold the back in a supported position. The specific use of the pad will be described in greater detail below.

It should also be appreciated that the loops could be formed by straps terminating at the edges of the back support member as long as the mechanical connection between the straps and the back support member is of sufficient strength to withstand the forces subjected to it during use.

Figure 4:
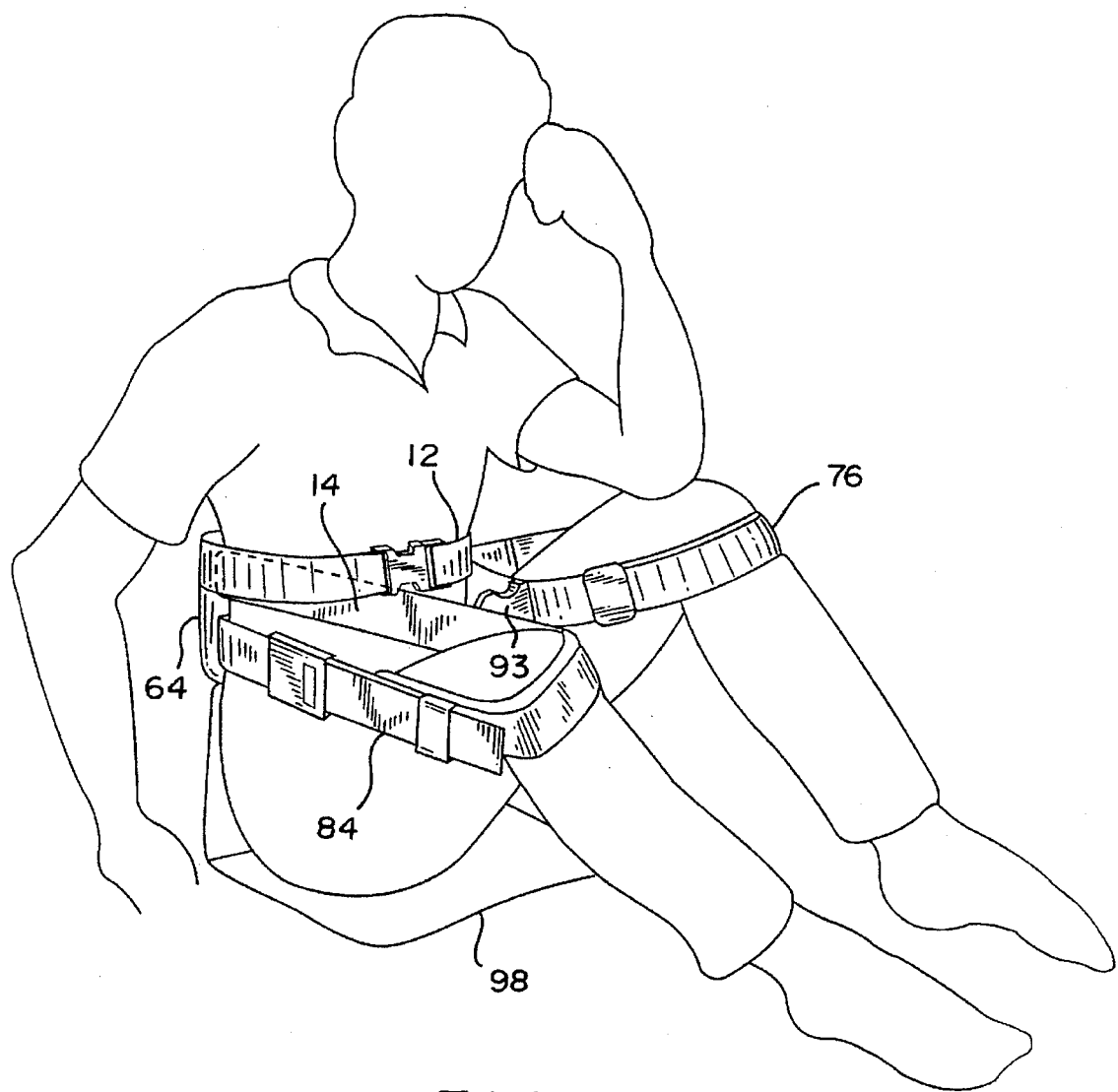
FIG. 4 is a perspective view of an individual utilizing the present waist supported carrying case.

A connector member 93 in the form of a latching type buckle having a male locking member 94 and a female locking member 96 is also provided. The male locking member 94 is secured along the first end 72 of the second strap 68 and the female locking member 96 is secured along the second end 80 of second strap 68. The male locking member 94 and the female locking member 96 are positioned to be connected on the inner sections of the first and second loops. As shown in FIG. 4, when the back support 62 is used, the male locking member 94 and the female locking member 96 may be latched. This connects the inner sections of the loops to maintain the user's knees together in a more comfortable position. Positioning the knees in this manner further relieves the strain on the lower back and aids in positioning the back support member in the proper position. It will be appreciated that other connecting means such as hooks, clips, latches, elastic bands or the like may be used with equal effectiveness to hold the strap loops together.

The central sleeve 36 is also provided with a seat pad 98 that may be folded out when the central sleeve 36 is opened. The seat pad 98 is provided such that an individual may sit on the pad while using the back support 62.

The back support member 64 is held about the waist of user by the first belt member 12 and the second belt member 14. As discussed above, the first belt member 12 and the second belt member 14 are adapted to encircle the waist of the user. The first belt member 12 and the second belt member 14 are secured about the user's waist by cooperating locking members 22, 24 so that the back support 62 is worn on the user without the necessity of having the first loop 76 and second loop 84 passing over the knees to maintain the back support member in place. Although this does not provide any supporting function, it eliminates the need for repositioning the support each time that it is used. It also permits removal of the knees during activities without having to interrupt the particular activity to handle or store the back support.

Figure 5:
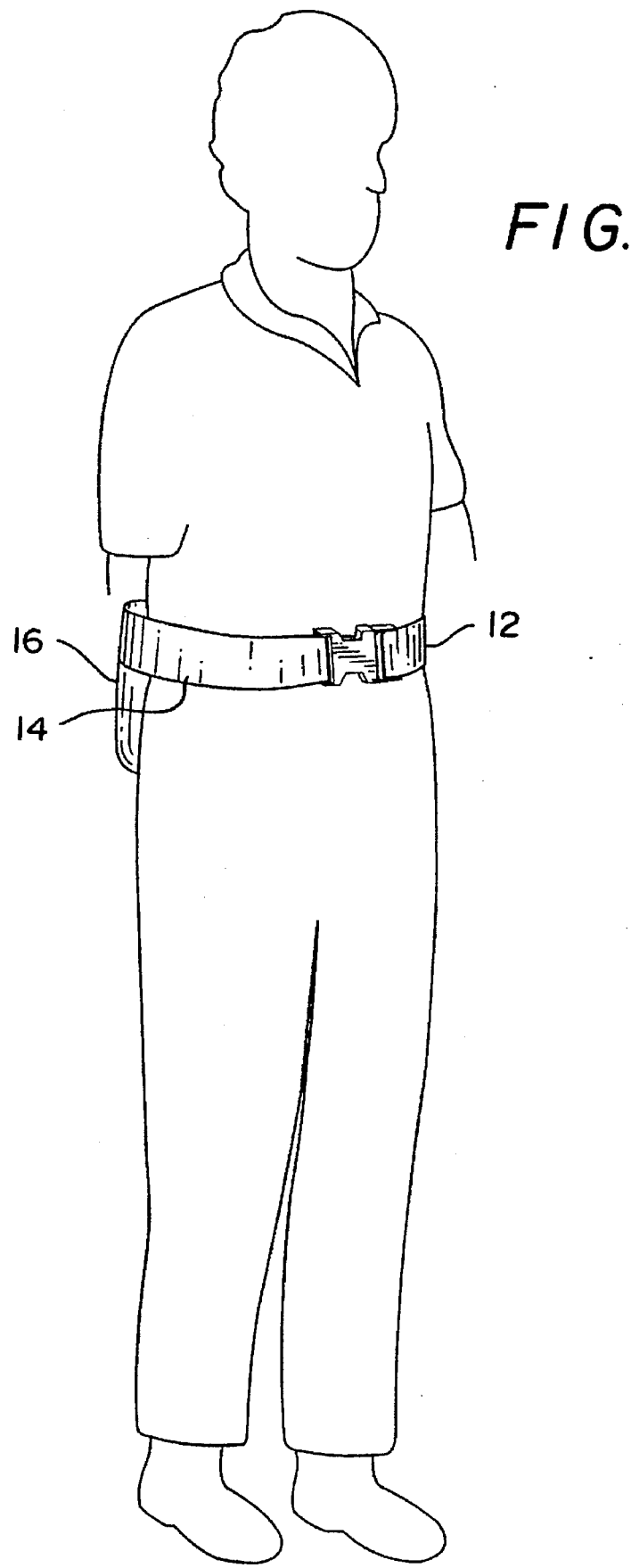
FIG. 5 is a perspective view of an individual wearing the present waist supported carrying case without the central sleeve opened.

Referring to FIG. 4, a user is shown wearing the back support 62. The back support member 64 is fit against the lumbar portion of the back. The first loop 76 and second loop 84 are passed over the knees with the user in a seated position. The connecting member 93 keeps the knees of the user together. Force, exerted by the knees, pulls the back support member 64 against the lumbar region of the wearer's back to provide suitable support. When not in use, the straps are folded into the integrally formed carrying case as described hereinabove. The carrying case 10 is shown in its non-use configuration in FIG. 5.

Figure 6:
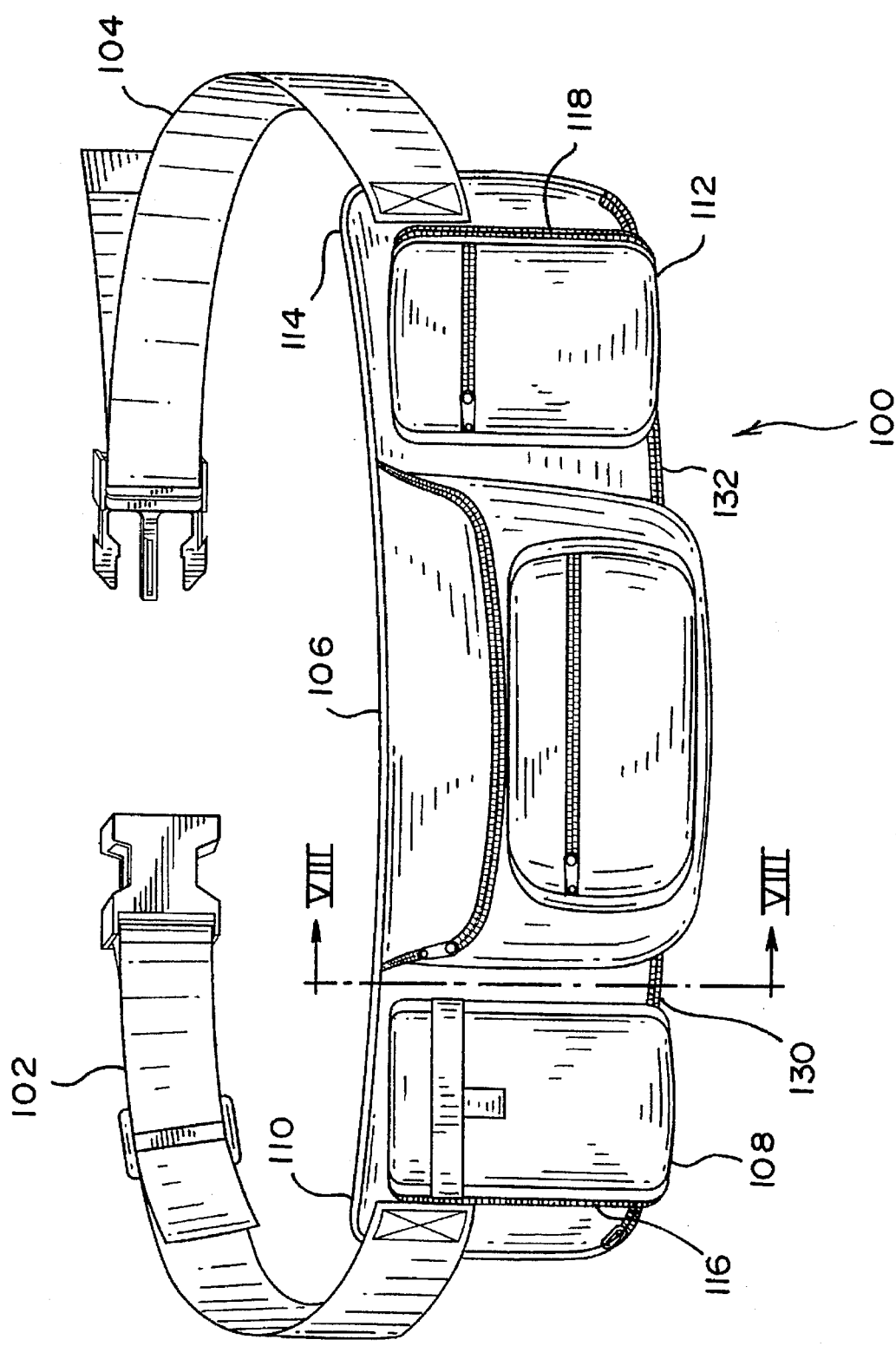
FIG. 6 is a perspective view of an alternate embodiment of the present invention.
Figure 7:
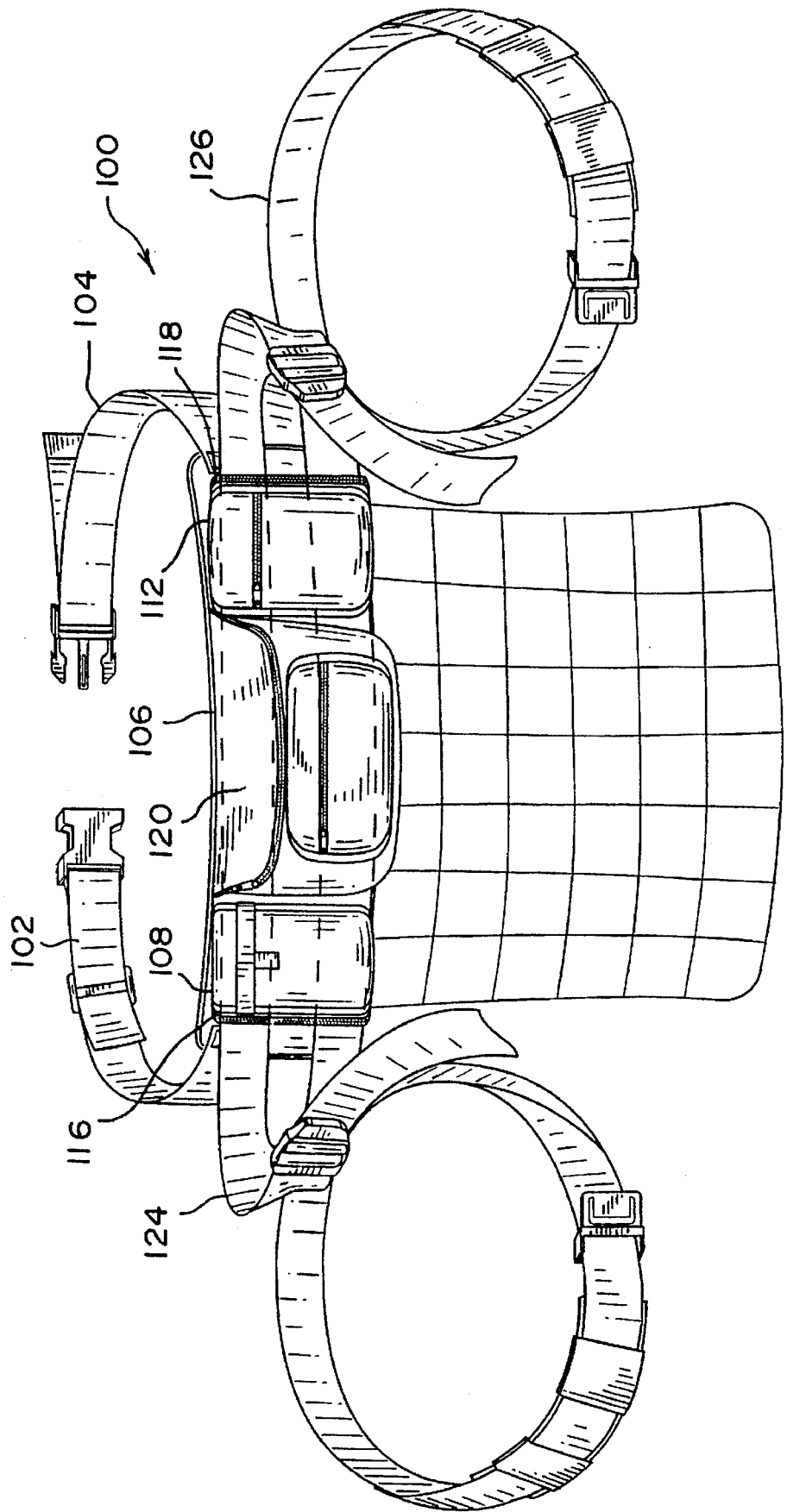
FIG. 7 is a perspective view of the alternate embodiment with the back support removed for use.
Figure 8:
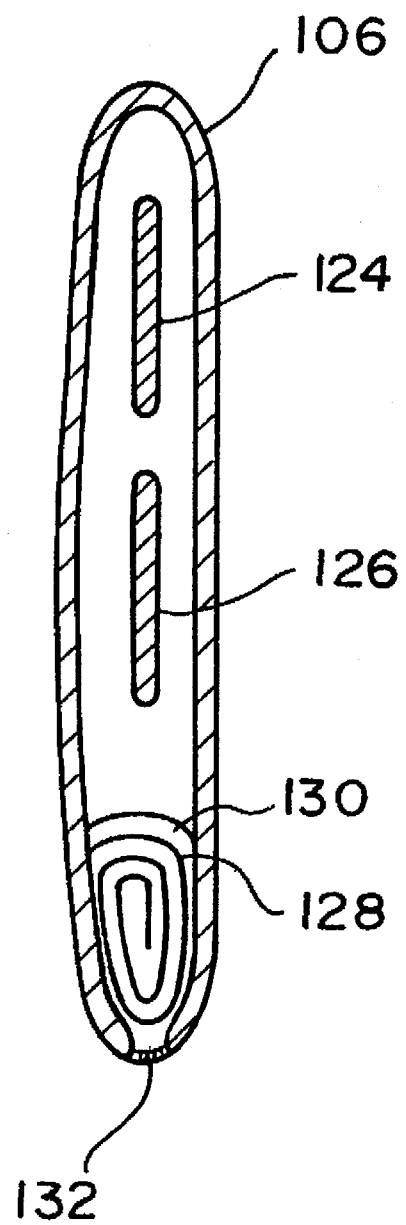
FIG. 8 is a cross-sectional view through Section VIII— VIII as shown in FIG. 6.

An alternate embodiment of the present invention is shown in FIGS. 6–8. As with the embodiment disclosed above, a conventional waist supported carrying case 100 is provided. The waist supported carrying case 100 includes a first belt member 102, a second belt member 104, and a pouch assembly 106. However, the pouch assembly 106 is provided with a first pocket 108 at the first end 110 of the pouch assembly 106 adjacent the attachment between the first belt member 102 and the pouch assembly 106. The pouch assembly 106 is also provided with a second pocket 112 at the second end 114 of the pouch assembly 106 adjacent the attachment between the second belt member 104 and the pouch assembly 106. The first pocket 108 and the second pocket 112 each include an opening 116, 118 that may be selectively closed through the provision of a zipper. Although the disclosed embodiment is provided with a zipper for selectively opening and closing the first pocket and the second pocket, other well known closure devices could be employed without departing from the spirit of the present invention.

The first pocket 108 and the second pocket 112 provide access to a sleeve 120 formed within the pouch assembly 106. That is, the sleeve defines an open space between the opening 116 formed in the first pocket 108 and the opening 118 formed in the second pocket 112. As such, a back support such as those disclosed in my U.S. Pat. Nos. 4,773,106, 4,813,080, and 5,001,791, incorporated herein by reference, may be stored within the waist supported carrying case 10.

The stored back support 122 may be withdrawn for use by simply opening the first pocket 108 and the second pocket 112, and withdrawing the straps 124, 126 of the back support. It should be understood that the back support may be used while it is held within the sleeve. Alternately, the back support may be entirely removed from the waist supported carrying case and used in the manner described in my prior patents while the pouch assembly of waist supported carrying case is rotated and worn on the stomach of the individual.

As with the embodiment disclosed in FIGS. 1 to 5, the waist supported carrying case 100 is provided with an integral seat pad 128. The seat pad 128 is stored within a seat pad sleeve 130 formed in the pouch assembly 106. Specifically, the seat pad sleeve 130 is formed in the central portion of the pouch assembly 106. The seat pad sleeve 130 is opened and closed by a zipper 132 on the outer surface of the pouch assembly 106. When the zipper 132 is moved to its open position, the seat pad sleeve 130 is opened to reveal the seat pad 128 stored within the seat pad sleeve 130.

Other modifications or alterations to the above described invention may be made. For example, the back support may be made of rigid or semi-rigid sections and specific individuals could be fitted with supports that are molded exactly to their body contours. As indicated above, the size of the back support section and the straps may be adjusted for various users in keeping within the scope and spirit of the present invention as defined in the following claims.

While the preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. A waist supported carrying case including a therapeutic back support for supporting the lower back region of a user in a seated position, comprising:

a belt for securing the carrying case to the waist of an individual;

a pouch assembly positioned on the belt, wherein the pouch assembly includes at least one pocket secured to the outside of the pouch assembly providing an individual with a storage compartment and at least one sleeve having a therapeutic back support therein, the therapeutic back support being selectively positioned within the at least one sleeve when the therapeutic back support is in its storage position and removed from within the at least one sleeve when the therapeutic back support is in its use position; and wherein the belt may be secured to the waist of an individual whether the therapeutic back support is in its storage position or its use position.

2. The carrying case according to claim 1, wherein the back support is integrally formed within the at least one sleeve.

3. The carrying case according to claim 2, wherein the back support includes a rectangular back supporting member secured to the pouch assembly, the back support member having a length substantially spanning the width of the lower back of the user and a width substantially spanning the height of the lumber portion of the user, the back support further including elongated straps attached to and extending from the pouch assembly, the straps forming loops and being of such a length to engage the knees of the user when the user is in a seated position whereby the force of the knees of the user on the straps pulls the back supporting member against the back of the user, supporting the back.

4. The carrying case according to claim 2, wherein a seat pad is integrally stored within the at least one sleeve.

5. The carrying case according to claim 2, wherein the pouch assembly includes means for opening and closing the at least one sleeve to selective utilize the back support member.

6. The carrying case according to claim 1, wherein the back support includes a rectangular back supporting member secured to the pouch assembly, the back support member having a length substantially spanning the width of the lower back of the user and a width substantially spanning the height of the lumber portion of the user, the back support further including elongated straps attached to and extending from the pouch assembly, the straps forming loops and being of such a length to engage the knees of the user when the user is in a seated position whereby the force of the knees of the user on the straps pulls the back supporting member against the back of the user, supporting the back.

7. The carrying case according to claim 1, wherein the pouch assembly is also provided with a seat pad.

8. The carrying case according to claim 1, wherein the back support is removably stored within the at least one sleeve.

9. The carrying case according to claim 8, wherein the pouch assembly includes means for opening and closing the at least one sleeve to selective utilize the back support member.

10. The carrying case according to claim 8, wherein the back support includes a generally rectangular back supporting member having a length substantially spanning the width of the lower back of the user and a width substantially spanning the height of the lumber portion of the user, elongated straps attached to and extending from the ends of the back supporting member, the straps forming loops being of such a length to engage the knees of the user when the user is in a seated position whereby the force of the knees of the user on the straps pulls the back supporting member against the back of the user, supporting the back of the user.

11. The carrying case according to claim 8 wherein a seat pad is integrally stored within the pouch assembly.

12. The carrying case according to claim 1, wherein the pouch assembly includes a plurality of pockets for storing items.

13. The carrying case according to claim 1, wherein the pocket assembly is secured between a first belt member and a second belt member, and the first belt member and the second belt member are respectively provided with cooperating locking members for securing the carrying case about the waist of a user.

14. A method for supporting the lumbar region of a user in a seated position, comprising the following steps:

positioning a carrying case about the waist of a user, wherein the carrying case includes at least one pocket secured to the outside of the pouch assembly providing an individual with a storage compartment and at least one sleeve having a therapeutic back support therein for supporting the lower back region of a user in a seated position, the therapeutic back support being selectively positioned within the at least one sleeve when the therapeutic back support is in its storage position and removed from within the at least one sleeve when the therapeutic back support is in its use position such that the belt may be secured to the waist of an individual whether the therapeutic back support is in its storage position or its use position, and the back support includes a generally rectangular supporting member having a length substantially spanning the width of the lower back of the user and a width substantially spanning the height of the lumber portion of the user, elongated straps attached to and extending from the ends of the back supporting member, the straps forming loops being of such a length to engage the knees of the user when the user is in a seated position whereby the force of the knees of the user on the straps pulls the back supporting member against the back of the user, supporting the back of the user;

locating the support member on the lumbar region of the user;

positioning the straps about the knees of the user;

exerting an outward force with the knees against the straps to thereby pull the support member against the lumbar region and support the lumber region.

15. The method according to claim 14, wherein the back support is integrally formed with the pouch assembly.

16. The method according to claim 15, wherein the back support member is secured to the pouch assembly.

17. The method according to claim 14, wherein the back support is releasably stored within the pouch assembly.

18. The method according to claim 14, wherein a seat pad is integrally stored within the pouch assembly, and the method includes the additional steps of removing the seat pad from the pouch assembly and sitting on the seat pad while the straps a positioned about the knees of the user.

19. A waist supported carrying case, comprising:

a belt for securing the carrying case to the waist of an individual;

a pouch assembly positioned on the belt, the pouch assembly including at least one pocket secured to the outside of the pouch assembly providing an individual with a storage compartment and at least one sleeve having a seat pad secured to, and stored within, the at least one sleeve, the seat pad being stored such that the seat pad may be withdrawn from the pouch assembly and positioned between an individual and a support surface when the individual plans to sit; and wherein the seat pad is selectively positioned within the at least one sleeve when the seat pad is in its storage position and removed from within the at least one sleeve when the seat pad is in its use position such that the belt may be secured to the waist of an individual whether the seat pad is in its storage position or its use position.

20. The waist supported carrying case according to claim 19, wherein the sleeve includes means for selectively opening and closing the sleeve to permit an individual to control access to the seat pad.

* * * * *